(12) United States Patent
Matsukura et al.

(10) Patent No.: US 10,983,085 B2
(45) Date of Patent: Apr. 20, 2021

(54) GAS SENSOR

(71) Applicant: NGK SPARK PLUG CO., LTD., Nagoya (JP)

(72) Inventors: Yusuke Matsukura, Nagoya (JP); Shoji Kitanoya, Kasugai (JP); Masaya Watanabe, Komaki (JP); Daisuke Ichikawa, Minokamo (JP); Masahiro Yamashita, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 22 days.

(21) Appl. No.: 16/050,787

(22) Filed: Jul. 31, 2018

(65) Prior Publication Data

US 2019/0041353 A1  Feb. 7, 2019

(30) Foreign Application Priority Data

Aug. 2, 2017 (JP) .............................. JP2017-149988
Mar. 22, 2018 (JP) .............................. JP2018-054440

(51) Int. Cl.
*G01N 27/407* (2006.01)
*G01N 33/00* (2006.01)
*G01N 27/16* (2006.01)

(52) U.S. Cl.
CPC ......... *G01N 27/4077* (2013.01); *G01N 27/16* (2013.01); *G01N 27/4071* (2013.01);
(Continued)

(58) Field of Classification Search
CPC . G01N 27/4078; G01N 27/16; G01N 27/4077
See application file for complete search history.

(56) References Cited

U.S. PATENT DOCUMENTS 4,326,214 A * 4/1982 Trueblood ............. G11C 16/18
                                                      174/544
2005/0217370 A1* 10/2005 Takahashi ......... G01N 33/0009
                                                      73/431
(Continued)

FOREIGN PATENT DOCUMENTS

JP      2001-124716 A      5/2001
JP      2006-126160 A      5/2006
(Continued)

OTHER PUBLICATIONS

JP2001-124716 machine translation (Year: 2001).*
(Continued)

*Primary Examiner* — Luan V Van
*Assistant Examiner* — Caitlyn Mingyun Sun
(74) *Attorney, Agent, or Firm* — Sughrue Mion, PLLC

(57) ABSTRACT

Disclosed is a gas sensor for detecting a measurement target gas in a measurement gas atmosphere, including: a first sensor element; a first installation part defining a first inner space in which the first sensor element is installed; and a casing accommodating therein the first installation part. The casing has an opening formed to introduce the measurement target gas into an inside of the casing. The first installation part has: a first gas introduction hole formed to provide communication between the first inner space and the inside of the casing; and a membrane member arranged to cover the first gas introduction hole and having permeability to water vapor and substantially no permeability to the measurement target gas. At least a portion of the first installation part in contact with the membrane member is made of insulating ceramic material or resin material.

12 Claims, 9 Drawing Sheets

(52) U.S. Cl.
CPC ..... *G01N 27/4074* (2013.01); *G01N 27/4078* (2013.01); *G01N 33/006* (2013.01); *G01N 33/0027* (2013.01)

(56) References Cited

U.S. PATENT DOCUMENTS

| | | | |
|---|---|---|---|
| 2011/0139618 A1* | 6/2011 | Serrels | G01N 27/4071 204/408 |
| 2011/0168557 A1* | 7/2011 | Park | G01N 27/4074 204/424 |
| 2015/0226688 A1* | 8/2015 | Watanabe | G01N 27/18 73/31.05 |

FOREIGN PATENT DOCUMENTS

| | | | | |
|---|---|---|---|---|
| JP | 2010-237007 A | | 10/2010 | |
| JP | 2015-148540 A | | 8/2015 | |
| JP | 2006126160 | * | 5/2016 | ............. G01N 27/16 |

OTHER PUBLICATIONS

JP 2001-124716 machine translation version (Year: 2001).*
JP 2010237007 machine translation version (Year: 2010).*
Communication issued Jan. 5, 2021 by the Japanese Patent Office in application No. 2018-054440.

\* cited by examiner

GAS SENSOR

FIELD OF THE INVENTION

The present invention relates to a gas sensor.

BACKGROUND OF THE INVENTION

There is known a gas sensor capable of detecting and measuring a specific measurement target gas such as combustible gas in a measurement gas atmosphere without being influenced by water (see, for example, Japanese Laid-Open Patent Publication No. 2001-124716). This gas sensor has a pair of first and second sensor elements installed in first and second separate inner spaces. The first inner space in which the first sensor element (as a reference sensor element) is installed is in communication with the measurement gas atmosphere via a membrane member, whereas the second inner space in which the second sensor element (as a detection sensor element) is installed is open to the measurement gas atmosphere. The membrane member is of the type having permeability to water vapor but no permeability to the measurement target gas, as typified by an ion-exchange membrane. In such a configuration, both of the first and second sensor elements are placed under the same humidity conditions so as to enable detection and measurement of the measurement target gas without being influenced by humidity.

SUMMARY OF THE INVENTION

The above disclosed gas sensor is provided with a mount base and a cap such that the first inner space for installation of the first sensor element is defined between the mount base and the cap. If there is a large difference in thermal expansion coefficient between the mount base and the cap, the joint of the mount base and the cap may be broken by a thermal shock to cause a deterioration in the sealing of the first inner space. Further, the water vapor permeability of the membrane member is deteriorated by metal ions. If a portion of the cap in contact with the membrane member is formed using a metal material, the output of the gas sensor tends to be influenced by humidity due to loss of the function of the membrane member.

It is accordingly an object of the present invention to provide a gas sensor in which a sensor element is installed in an inner space communicating with a measurement gas atmosphere via a membrane member so as to improve the sealing of the inner space and suppress a deterioration in the water vapor permeability of the membrane member.

In accordance with a first aspect of the present invention, there is provided a gas sensor for detecting a measurement target gas in a measurement gas atmosphere, comprising:
a first sensor element;
a first installation part defining a first inner space in which the first sensor element is installed; and
a casing accommodating therein the first installation part,
the casing having an opening formed to introduce the measurement target gas into an inside of the casing,
the first installation part having: a first gas introduction hole formed to provide communication between the first inner space and the inside of the casing; and a membrane member arranged to cover the first gas introduction hole and having permeability to water vapor and substantially no permeability to the measurement target gas,
wherein at least a portion of the first installation part in contact with the membrane member is made of insulating ceramic material or resin material.

In this aspect, the portion of the first installation part in contact with the membrane member is made of an insulating ceramic material or a resin material. It is thus possible to improve the sealing of the first inner space in which the first sensor element (as a reference sensor element) is installed.

The gas introduction hole is formed in the first installation part, which is made of insulating ceramic material or resin material, and is covered by the membrane member, which is permeable to water vapor but substantially not permeable to the measurement target gas. Consequently, the membrane member is not in contact with a metal material and is prevented from contamination by metal ions. It is thus possible to suppress a deterioration in the water vapor permeability of the membrane member.

In accordance with a second aspect of the present invention, there is provided a gas sensor as described above, wherein the first installation part is made of an insulating ceramic material.

In this aspect, it is possible to further improve the sealing of the first inner space while suppressing a deterioration in the water vapor permeability of the membrane member.

In accordance with a third aspect of the present invention, there is provided a gas sensor as described above, wherein the first installation part is constituted by: a mount base made of an insulating ceramic material so as to mount thereon the first sensor element; and a protective cap made of an insulating ceramic material and disposed on the mount base so as to cover the mount base and define the first inner space between the mount base and the protective cap, and wherein the mount base and the protective cap are bonded together by an insulating adhesive.

In this aspect, it is possible to easily and reliably form the first installation part with the first inner space.

In accordance with a fourth aspect of the present invention, there is provided a gas sensor as described above, wherein the mount base and the protective cap are made of the same insulating ceramic material.

In this aspect, it is possible to more reliably improve the sealing of the first inner space as there is no difference in thermal expansion coefficient between the mount base and the protective cap.

In accordance with a fifth aspect of the present invention, there is provided a gas sensor as described above, wherein the insulating adhesive contains a thermosetting resin as a main component.

In this aspect, it is possible to effectively improve the adhesion of the mount base and the protective cap.

In accordance with a sixth aspect of the present invention, there is provided a gas sensor as described above, further comprising:
a second sensor element; and
a second installation part accommodated in the casing and defining a second inner space in which the second sensor element is installed,
wherein each of the first and second sensor elements has a heating resistor whose resistance value varies with change in temperature thereof, and
wherein the second installation part has a second gas introduction hole formed to allow direct introduction of the measurement target gas from the inside of the casing into the second inner space.

In this aspect, it is possible to obtain the gas sensor with high gas detection accuracy.

In accordance with a seventh aspect of the present invention, there is provided a gas sensor as described above, wherein the second installation part is constituted by the mount base and the protective cap, so that the second sensor element is mounted on the mount base, and so that the protective cap is disposed on the mount base so as to cover the mount base and define the second inner space between the mount base and the protective cap.

In this aspect, it is possible to simultaneously and easily form the first and the second installation parts. As the first and second inner spaces can be located close to each other, it is possible to reduce the temperature difference between these first and second inner spaces and suppress an error in the output of the gas sensor.

In accordance with an eighth aspect of the present invention, there is provided a gas sensor as described above, wherein the membrane member is an ion exchange membrane made of fluororesin.

In this aspect, it is possible to more reliably allow permeation of water vapor through the membrane member but not allow permeation of the measurement target gas.

In accordance with a ninth aspect of the present invention, there is provided a gas sensor as described above, wherein the first installation part comprises a measurement target gas oxidation catalyst that causes oxidation of the measurement target gas flowing into the first inner space.

In the case where the concentration of the measurement target gas is high, there may occur a phenomenon in which the output of the gas sensor slightly decreases with time despite no changes in the concentration of the measurement target gas (see FIG. 10). As a result of extensive researches, the present inventors have found that this sensor output decrease phenomenon takes place with increase in the concentration of the measurement target gas in the first installation part due to slight permeation of the measurement target gas through the membrane member.

In this aspect, however, the measurement target gas oxidation catalyst is arranged to oxide the measurement target gas. The measurement target gas, when passed through the membrane member under such a situation that the concentration of the measurement target gas is high, is oxidized by the measurement target gas oxidation catalyst and thereby removed from the first inner space. It is thus possible to, even in the case where the concentration of the measurement target gas is high, maintain a difference in the concentration of the measurement target gas between the first and second inner spaces and suppress a deterioration in the output of the gas sensor.

In accordance with a tenth aspect of the present invention, there is provided a gas sensor as described above, wherein the measurement target gas oxidation catalyst is arranged inside the first inner space and/or between the membrane member and the first inner space.

In this aspect, it is possible to more reliably remove the measurement target gas flowing into the first inner space.

In accordance with an eleventh aspect of the present invention, there is provided a gas sensor as described above, wherein the measurement target gas oxidation catalyst is arranged inside the first gas introduction hole.

In this aspect, the measurement target gas which has passed through the membrane member is efficiently brought into contact with the measurement target gas oxidation catalyst. It is thus possible to reliably suppress a deterioration in the output of the gas sensor.

In accordance with a twelfth aspect of the present invention, there is provided a gas sensor as described above, wherein the measurement target gas oxidation catalyst is arranged to cover the first gas introduction hole.

In this aspect, the measurement target gas which has passed through the membrane member is readily and efficiently brought into contact with the measurement target gas oxidation catalyst. It is thus more reliably suppress a deterioration in the output of the gas sensor.

In accordance with a thirteenth aspect of the present invention, there is provided a gas sensor as described above, wherein the measurement target gas oxidation catalyst is sheet-shaped and arranged on a first inner space-side surface of the membrane member.

In this aspect, it is possible to easily and reliably cover the first gas introduction hole by the measurement target gas oxidation catalyst as the membrane member and the measurement target gas oxidation catalyst are integrally laminated together.

In accordance with a fourteenth aspect of the present invention, there is provided a gas sensor as described above, wherein the first installation part comprises a sheet-shaped support member that supports at least one of the membrane member and the measurement target gas oxidation catalyst.

In this aspect, it is possible to suppress warpage of the membrane member and the measurement target gas oxidation catalyst and improve the sealing of the first gas introduction hole. It is also possible to improve the handling of the integrated sheet structure of the membrane member and the measurement target gas oxidation catalyst.

The other objects and features of the present invention will also become understood from the following description.

DESCRIPTION OF EMBODIMENTS

Hereinafter, embodiments of the present invention will be described below with reference to the drawings.

1-1. First Embodiment

A gas sensor 1 according to the first embodiment of the present invention will be now explained below with reference to FIGS. 1 to 5. The gas sensor 1 is herein configured to detect and measure a specific measurement target gas in a measurement gas atmosphere. The measurement target gas detected and measured by the gas sensor 1 is a combustible gas such as hydrogen, ammonia, carbon monoxide (CO), hydrocarbon (HC) or the like.

Figure 1:
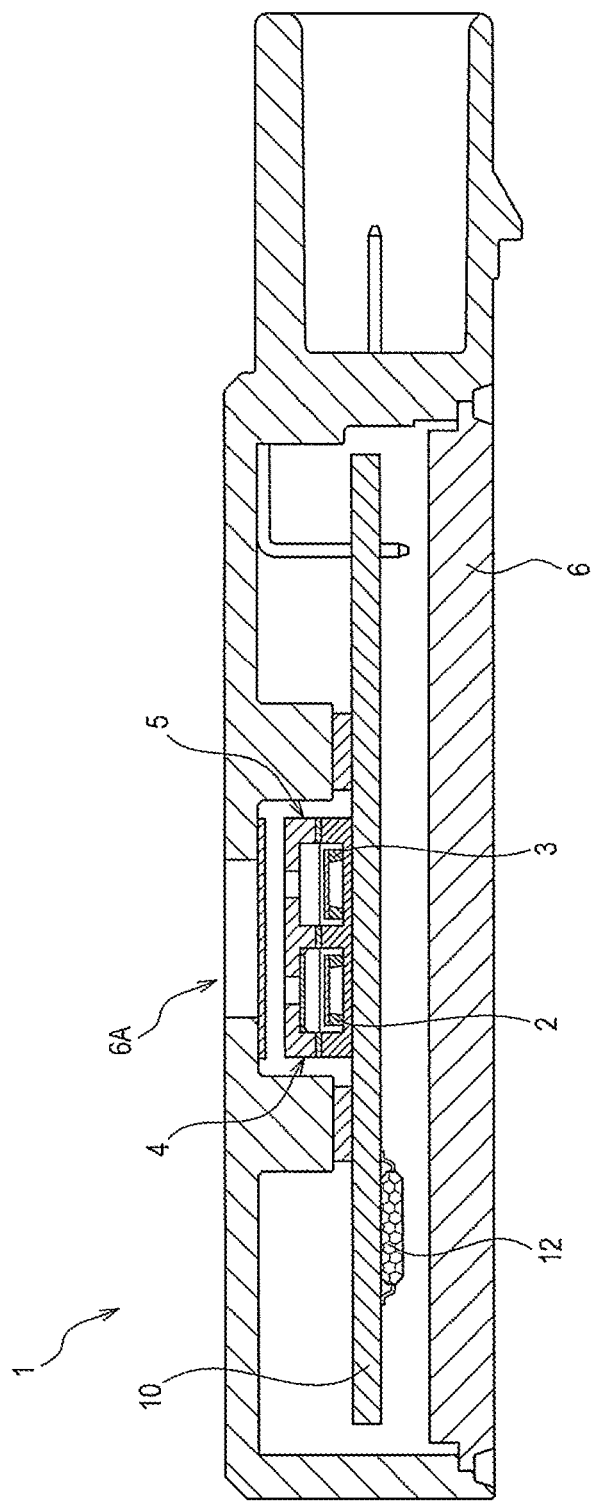
FIG. 1 is a schematic cross-sectional view of a gas sensor according to a first embodiment of the present invention.

As shown in FIG. 1, the gas sensor 1 includes a first sensor element 2, a second sensor element 3, a first installation part 4, a second installation part 5, a casing 6, a circuit board 10 and a calculation unit 12.

⟨First and Second Sensor Elements⟩

Figure 3:
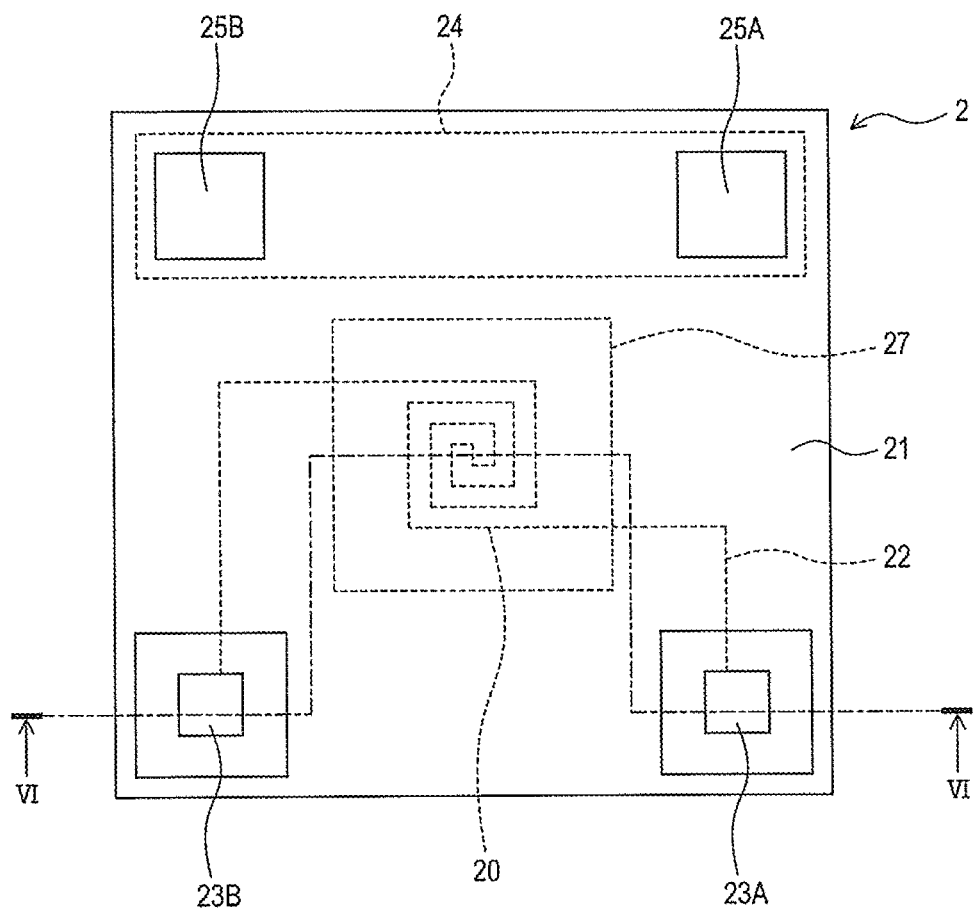
FIG. 3 is a schematic plan view of a sensor element of the gas sensor according to the first embodiment of the present invention.
Figure 4:
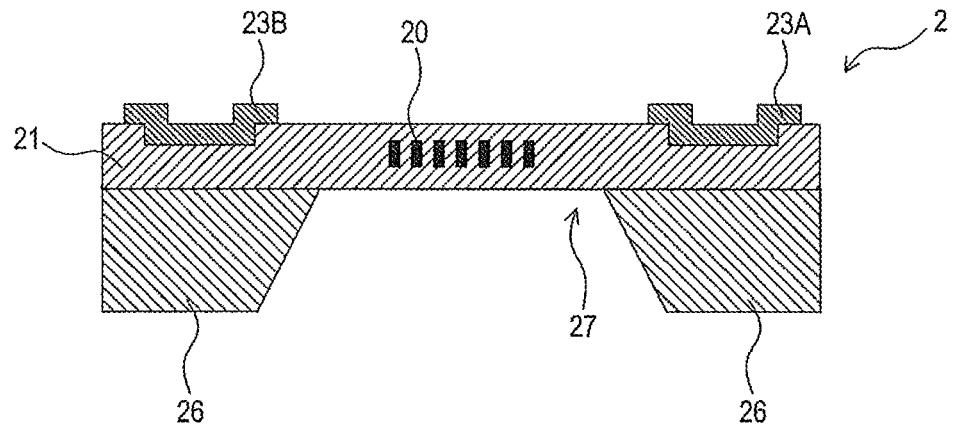
FIG. 4 is a schematic cross-sectional view of the sensor element as taken along line VI-VI of FIG. 3.

In the first embodiment, the first sensor element 2 is in the form of a thermal conductivity type sensor element that does not react with the measurement target gas. As shown in FIGS. 3 and 4, the first sensor element 2 includes a heating resistor 20, an insulating layer 21, a wiring 22, a pair of first electrode pads 23A and 23B, a temperature measuring resistor 24, a pair of second electrode pads 25A and 25B and a substrate 26.

The heating resistor 20 is provided as a spiral pattern conductor and is embedded in a center portion of the insulating layer 21. Further, the heating resistor 20 is electrically connected to the first electrode pads 23A and 23B via the wiring 22.

The first electrode pads 23A and 23B are disposed on one side of the insulating layer 21. One of the first electrode pads 23A and 23B is connected to a ground, whereas the other of the first electrode pads 23 and 23B is connected to the circuit board 10.

The substrate 26 is made of a silicon material and disposed on the other side of the insulating layer 21. As shown in FIG. 4, a hollow 27 is formed in the substrate 26 at a position corresponding to the heating resistor 20 so as to provide a diaphragm structure with the insulating layer 21 being exposed through the hollow 27.

The temperature measuring resistor 24 is embedded the insulating layer 20 at a position closer to the outer periphery than the heating resistor 20 (more specifically, embedded in one side portion of the insulating layer 21) and is electrically connected to the second electrode pads 25A and 25B.

The second electrode pads 25A and 25B are disposed on the same side of the insulating layer 21 as the first electrode pads 23A and 23B. One of the second electrode pads 25A and 25B is connected to a ground, whereas the other of the first electrode pads 23 and 23B is connected to the circuit board 10.

The heating resistor 20 is made of a conductive material having a high temperature resistance coefficient, and thus has a resistance value that varies with change in temperature thereof. For example, there can be used platinum (Pt) as the material of the heating resistor 20. The temperature measuring resistor 24 is made of a conductive material whose resistance value varies in proportion to temperature. There can be used the same material as the material of the heating resistor 20, such as platinum (Pt), as the material of the temperature measuring resistor 24. The wiring 22, the first electrode pads 23A and 23B and the second electrode pads 25A and 25B can also be made of the same material as the material of the heating resistor 20. The insulating layer 21 can be made of a single insulating material or can be made of different kinds of insulating materials in a multilayer structure. As the insulating material of the insulating layer 21, there can be used silicon oxide ($SiO_2$), silicon nitride ($Si_3N_4$) or the like.

As in the case of the first sensor element 2, the second sensor element 3 includes a heating resistor 30 whose resistance value varies with change in temperature. Since the second sensor element 3 has the same structure as that of the first sensor element 2 in the first embodiment, a detailed explanation of the structure of the second sensor element 3 will be omitted herefrom.

It is preferable that the resistance value of the heating resistor 21 of the first sensor element 2 is equal to that of the second sensor element 3.

⟨First and Second Installation Parts⟩

The first installation part 4 has a first inner space 4A, a first gas introduction hole 4B and a membrane member 4C.

The first inner pace 4A is defined in the first installation part 4 such that the first sensor element 2 is installed in the first inner space 4A. The first gas introduction hole 4B is formed in the first installation part 4 so as to provide communication between the first inner space 4A and the inside of the casing 6.

The membrane member 4C is arranged to cover the whole of the first gas introduction hole 4B. Herein, the membrane member 4C shows permeability to water vapor but substantially no permeability to the measurement target gas. The expression "substantially no permeability" means that the amount of permeation of the measurement target gas (on a volume basis) is less than or equal to 1/50 of the amount of permeation of water vapor. As the membrane member 4C, there can suitably be used a fluororesin-based ion exchange membrane. Specific examples of the fluororesin-based ion exchange membrane usable as the membrane member 4C are those available under the trade names of Nafion, Flemion, Aciplex and the like. As the membrane member 4C, there can alternatively be used a hollow fiber membrane capable of separating the measurement target gas and water vapor from each other.

Accordingly, the measurement target gas is not supplied into the first inner space 4A. The first sensor element 2 installed in the first inner space 4A serves as a reference sensor electrode without being exposed to the measurement target gas. The first sensor element 2 is however placed under the same humidity conditions as the second sensor element 3 because water vapor passes through the membrane member 4C.

The first installation part 4 has no opening other than the first gas introduction hole 4B.

On the other hand, the second installation part 5 has a second inner space 5A and a second gas introduction hole 5B.

The second inner pace 5A is defined in the second installation part 5 such that the second sensor element 3 is installed in the second inner space 5A. The second gas introduction hole 5B is formed in the second installation part 5 so as to provide communication between the second inner space 5A and the inside of the casing 6.

As the second gas introduction hole 5B is not covered by a membrane member and is open to the measurement gas atmosphere, the measurement target gas is supplied from the inside of the casing 6 into the second inner space 5A through the second gas introduction hole 5B. In other words, the second gas introduction hole 5A enables direct introduction of the measurement target gas into the second inner space 5A.

The second installation part 5 also has no opening other than the second gas introduction hole 5B.

Figure 2:
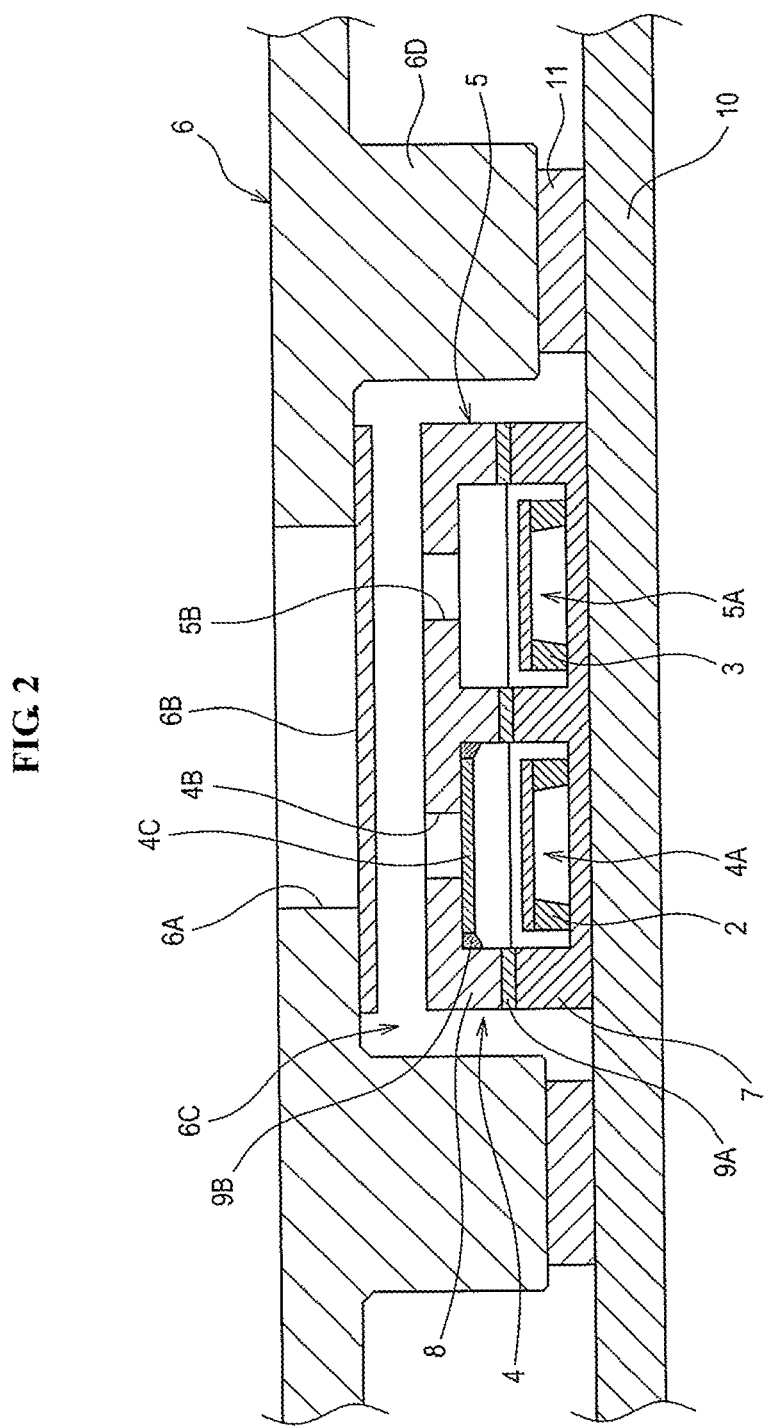
FIG. 2 is an enlarged cross-sectional of a part of the gas sensor in the vicinity of first and second installation parts according to the first embodiment of the present invention.

In the first embodiment, the first and second installation parts 4 and 5 are constituted by a common mount base 7 and a common protective cap (or cover) 8, each of which is made of an insulating ceramic material, as shown in FIGS. 1 and 2. Namely, the first and second inner spaces 4A and 5A are separately and adjacently defined, with a partition wall formed therebetween, by mounting the protective cap 8 on the mount base 7.

The mount base 7 is disposed on a surface of the circuit board 10 and is formed with two recess portions in which the first and second sensor elements 2 and 3 are respectively mounted.

The protective cap 8 is formed with two recess portions such that the recess portions of the protective cap 8 are opposed to and face the recess portions of the mount base 7 so as to define therebetween the first and second inner spaces 4A and 5A. The first and second gas introduction holes 4B and 5B are formed through the respective recess portions of the protective cap 8.

Each of the mount base 7 and the protective cap 8 is made of an insulating ceramic material as mentioned above in the first embodiment. As the ceramic material of the mount base 7, there can suitably be used alumina, aluminum nitride, zirconia or the like. As the ceramic material of the protective cap 8, there can suitably be used alumina or the like. In the first embodiment, the mount base 7 and the protective cap 8 are made of the same insulating material.

The protective cap 8 is bonded to the mount base 7 so that the mount base 7 and the first and second sensor elements 2 and 3 mounted in the recess portions of the mount base 7 are covered by the protective cap 8. In the first embodiment, the mount base 7 and the protective cap 8 are bonded together by an insulating adhesive 9A. As the insulating adhesive 9A, there can be used any insulating adhesive containing a thermosetting resin, thermoplastic resin or the like as a main component. For improvement of adhesion between the mount base 7 and the protective cap 8, it is preferable to use an insulating adhesive containing a thermosetting resin as a main component. Specific examples of the thermosetting resin usable in the insulating adhesive are epoxy resin and polyolefin resin. Herein, the expression "main component" means a component contained in an amount of 80 mass % or more.

In the first embodiment, the membrane member 4C is bonded by an insulating adhesive 9B to an inner surface of the protective cap 8 facing the first sensor element 2 and thus is fixed over an opening of the first gas introduction hole 4B close to the first inner space 4A. The insulating adhesive 9B for bonding of the membrane member 4C to the protective cap 8 can be the same as the insulating adhesive 9A for bonding of the protective cap 8 to the mount base 7.

⟨Casing⟩

The casing 6 is adapted to accommodate therein the first and second installation parts 4 and 5. The casing 6 has: a casing body formed with an opening 6A for introduction of the measurement target gas into the inside of the casing 6; and a filter 6B arranged in the opening 6A.

More specifically, the casing 6 includes an inner frame portion 6D protruding inward from an inner surface of the casing body so that the circuit board 10 is fixed to the inner frame portion 6D of the casing 6 via a seal member 11 to define therebetween an inner space 6C. The first and second installation parts 4 and 5 (that is, the mount base 7 and the protective cap 8) are accommodated in this inner space 6C.

The opening 6A is formed in the casing body so as to provide communication between the measurement gas atmosphere and the inner space 6C and introduce the measurement target gas into the inner space 6C. The measurement target gas introduced into the inner space 6C is supplied only to the second inner space 5A through the second gas introduction hole 5B. On the other hand, water vapor in the inner space 6C is diffused into both of first and second inner spaces 4A and 5A.

The filter 6B is provided as a water-repellent filter that allows permeation of the measurement target gas but does not allow permeation of water in liquid form (i.e. removes liquid water contained in the measurement target gas). By the arrangement of such a water-repellent filter 6B, the entry of liquid water into the inner space 6C can be prevented. In the first embodiment, the filter 6B is attached to the inner surface of the casing 6 (casing body) so as to cover the opening 6A.

⟨Circuit Board⟩

The circuit board 10 is plate-shaped and disposed inside the casing 6. The circuit board 10 has a circuit system equipped with a differential amplifier and fixed resistors $R_3$ and $R_4$ as shown in FIG. 5 and electrically connected to the respective electrode pads 23A, 23B, 25A and 25B of the sensor elements 2 and 3.

⟨Calculation Unit⟩

The calculation unit 12 is adapted to calculate the concentration D of the target measurement gas in the measurement gas atmosphere. As shown in FIG. 5, the heating resistor 20 of the first sensor element 2 and the heating resistor 30 of the second sensor element 30 are connected in series to each other; and the fixed resistors $R_3$ and the $R_4$ are connected in series with each other and arranged in parallel with the heating resistors 20 and 30. With the application of a constant voltage Vcc between the heating resistors 20 and 30, there develop a potential between the heating resistors 20 and 30 and a potential between the fixed resistors $R_3$ and $R_4$. A difference between these potentials is amplified and outputted as a potential difference Vd by the differential amplifier. The concentration D of the measurement target gas is calculated based on the potential difference Vd and outputted by the calculation unit 12.

Figure 5:
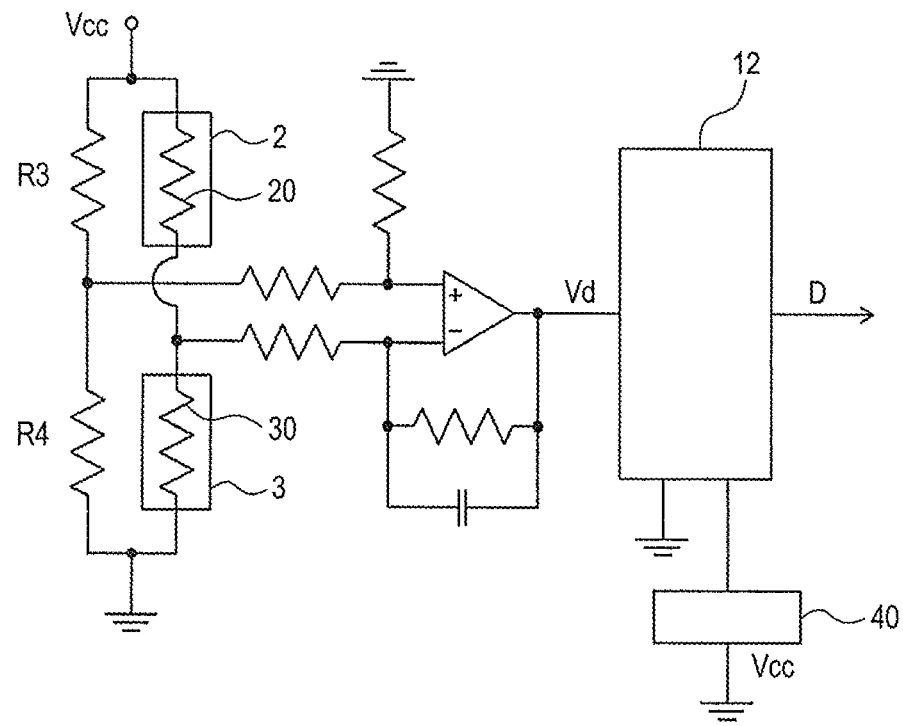
FIG. 5 is a schematic circuit diagram of the gas sensor according to the first embodiment of the present invention.

The calculation unit 12 and the circuit board 10 are herein supplied with current from a direct-current power supply 40 as shown in FIG. 5.

1-2. Effects

The following effects are obtained in the first embodiment.

(1a) Both of the mount base 7 and the protective cap 8, which define the first inner space 4A, are made of insulating ceramic materials so that the difference in thermal expansion coefficient between the mount base 7 and the protective cap 8 can be made small. It is consequently possible to prevent the adhesion of the mount base 7 and the protective cap 8 from becoming lowered due to a thermal shock and thereby possible to improve the sealing of the first inner space 4A in which the first sensor element 4 is installed as a reference sensor element.

(1b) The first gas introduction hole 4B is formed in the ceramic protective cap 8; and the membrane member 4C is attached to the ceramic protective cap 8 so as to cover the first gas introduction hole 4B. Hence, the membrane member 4C is not in contact with metal and is not contaminated by metal ions. It is thus possible to suppress a deterioration in the water vapor permeability of the membrane member.

(1c) In particular, the mount base 7 and the protective cap 8 are made of the same insulating ceramic material so that there is no difference in thermal expansion coefficient between the mount base 7 and the protective cap 8 in the first embodiment. It is thus possible to more reliably improve the sealing of the first inner space 4A.

(1d) Furthermore, not only the first installation part 4 but also the second installation part 5 are constituted by the mount base 7 and the protective cap 8 in the first embodiment. It is thus possible to simultaneously and easily form the first and the second installation parts 4 and 5. As the first and second inner spaces 4A and 5A can be located close to each other, it is possible to reduce the temperature difference between these first and second inner spaces 4A and 5A and suppress an error in the output of the gas sensor 1.

1-3. Second Embodiment

Figure 6:
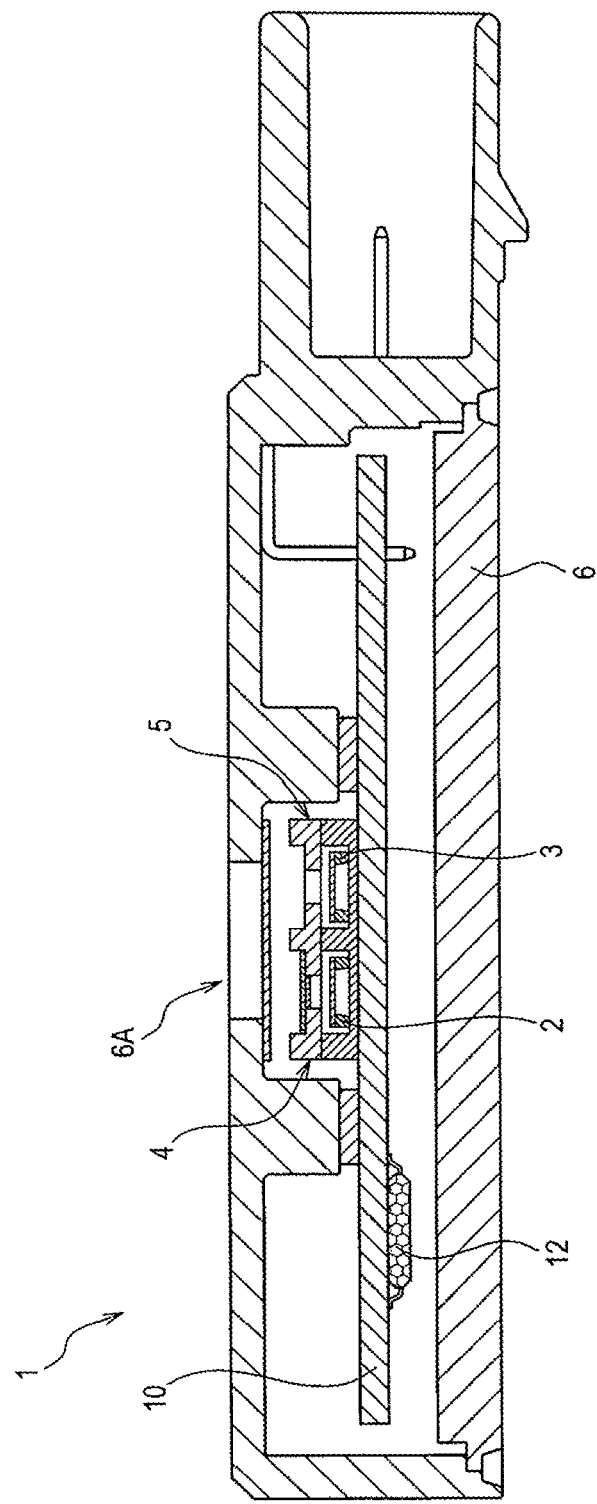
FIG. 6 is a schematic cross-sectional view of a gas sensor according to a second embodiment of the present invention.

The second embodiment of the present invention will be next explained below with reference to FIGS. 6 and 7. As shown in FIG. 6, the gas sensor 1 of the second embodiment is structurally the same as that of the first embodiment. Herein, the same configurations of the second embodiment as those of the first embodiment are designated by the same reference numerals to omit explanations thereof; and the following explanations will focus on differences between the first and second embodiments.

In the second embodiment, the gas sensor 1 is configured to detect and measure hydrogen gas (combustible gas) as the measurement target gas.

Figure 7:
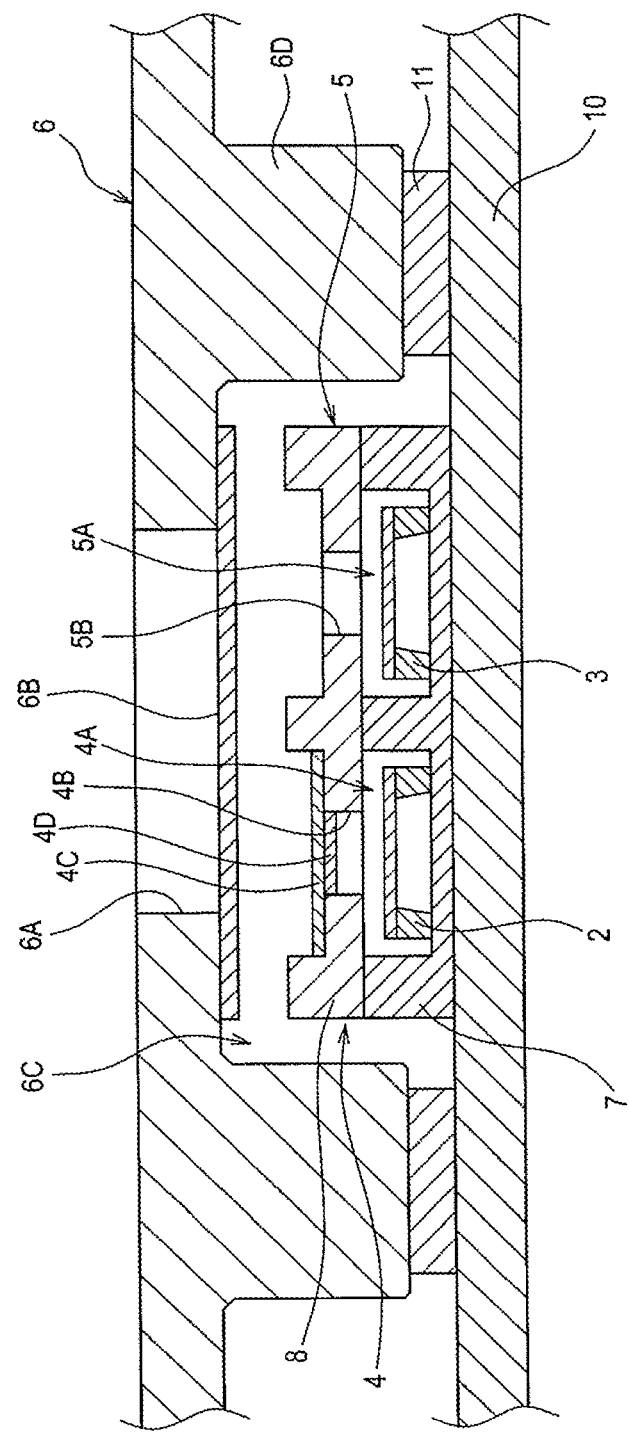
FIG. 7 is an enlarged cross-sectional of a part of the gas sensor in the vicinity of first and second installation parts according to the second embodiment of the present invention.

As shown in FIG. 7, the gas sensor 1 has a hydrogen oxidation catalyst 4D (as a measurement target gas oxidation catalyst) by which hydrogen gas flowing to the first inner space 4A is oxidized to water or water vapor. As such a hydrogen oxidation catalyst 4D, there can be used platinum, palladium, ruthenium, rhodium or alloy thereof. Among others, platinum or platinum-ruthenium alloy can preferably be used.

The hydrogen oxidation catalyst 4D is arranged between the membrane member 4C and the first inner space 4A. More specifically, the hydrogen oxidation catalyst 4D is arranged inside the first gas introduction hole 4B so as to cover the first gas introduction hole 4B. In other words, the hydrogen oxidation catalyst 4D is disposed so as to overlap in position with the first gas introduction hole 4B when viewed in the direction of axis of the first gas introduction hole 4B.

Further, the hydrogen oxidation catalyst 4D has a porous sheet shape by being supported on a support in the second embodiment. As such a catalyst support, there can be used activated carbon, fullerene, carbon nanohorn, carbon nanotube or the like. There can alternatively be used a porous ceramic material such as alumina or a metal material such as titanium as the support. This sheet-shaped hydrogen oxidation catalyst 4D is arranged on a surface of the membrane member 4C facing the first inner space 4A and then joined to the membrane member 4C by e.g. thermocompression bonding.

As the membrane member 4C and the hydrogen oxidation catalyst 4D are arranged to cover the first introduction hole 4B from the outside of the first inner space 4A in the second embodiment, it is feasible to dispose the membrane member 4C and the hydrogen oxidation catalyst 4D after defining the first inner space 4A by reflowing of the base 7 and the protective cap 8. The membrane member 4C and the hydrogen oxidation catalyst 4D are thus prevented from deformation due to expansion of air in the first inner space 4A during the reflowing. Alternatively, the membrane member 4C and the hydrogen oxidation catalyst 4D may be arranged to cover the first introduction hole 4B from the side of the first inner space 4A.

The membrane member 4C and the hydrogen oxidation catalyst 4D are placed in a recess portion of the protective cap 8, and are bonded and sealed at peripheries thereof to the protective cap 8 by an insulating adhesive.

In the high hydrogen concentration environment, hydrogen gas which has passed through the membrane member 4C is oxidized to water or water vapor by contact with the hydrogen oxidation catalyst 4D. As the humidity on the inner side (i.e. first inner space 4A-side) of the membrane member 4C becomes high, the water or water vapor is discharged out of the first inner space 4A via the membrane member 4C.

1-4. Effects

In the second embodiment, the following effects are also obtained.

(1e) In the case where the concentration of the hydrogen gas (as the measurement target gas) is high, the hydrogen gas which has passed through the membrane member 4C is oxidized by the hydrogen oxidation catalyst 4D and thereby removed from the first inner space 4A. It is thus possible to, even in the case where the concentration of the hydrogen gas in the measurement gas atmosphere is high, maintain a difference in the concentration of the hydrogen gas between the first inner space 4A (in which the first sensor element 2 is installed as a reference sensor element) and the second inner space 5A (in which the second sensor element 3 is installed as a detection sensor element) and suppress a deterioration in the output of the gas sensor 1.

(1f) As the hydrogen oxidation catalyst 4D is arranged inside the first gas introduction hole 4B so as to cover the first gas introduction hole 4B, hydrogen gas which has passed through the membrane member 4C is efficiently brought into contact with the hydrogen oxidation catalyst 4D. It is thus possible to more reliably suppress a deterioration in the output of the gas sensor 1.

(1g) Further, the hydrogen oxidation catalyst 4D is sheet-shaped and arranged on the first inner space 4A-side surface of the membrane member 4C so that the membrane member 4C and the hydrogen oxidation catalyst 4D can be integrated together. It is thus possible to easily and reliably cover the first gas introduction hole 4B by the hydrogen oxidation catalyst 4D.

1-5. Examples

In order to verify the effects of the second embodiments, Examples 1 and 2 were carried out by the following procedures.

In Example 2, a sample of the gas sensor 1 was produced as shown in FIG. 6. In Example 1, on the other hand, a sample of the gas sensor 1 was produced as shown in FIG. 6 but with no hydrogen oxidation catalyst 4D.

In each of Examples 1 and 2, the gas sensor 1 was placed in an environment of relative humidity 95% at 25° C. Then, 2 vol % of hydrogen gas was supplied to the gas sensor 1 for 15 minutes. The output of the gas sensor 1 was measured.

Figure 9:
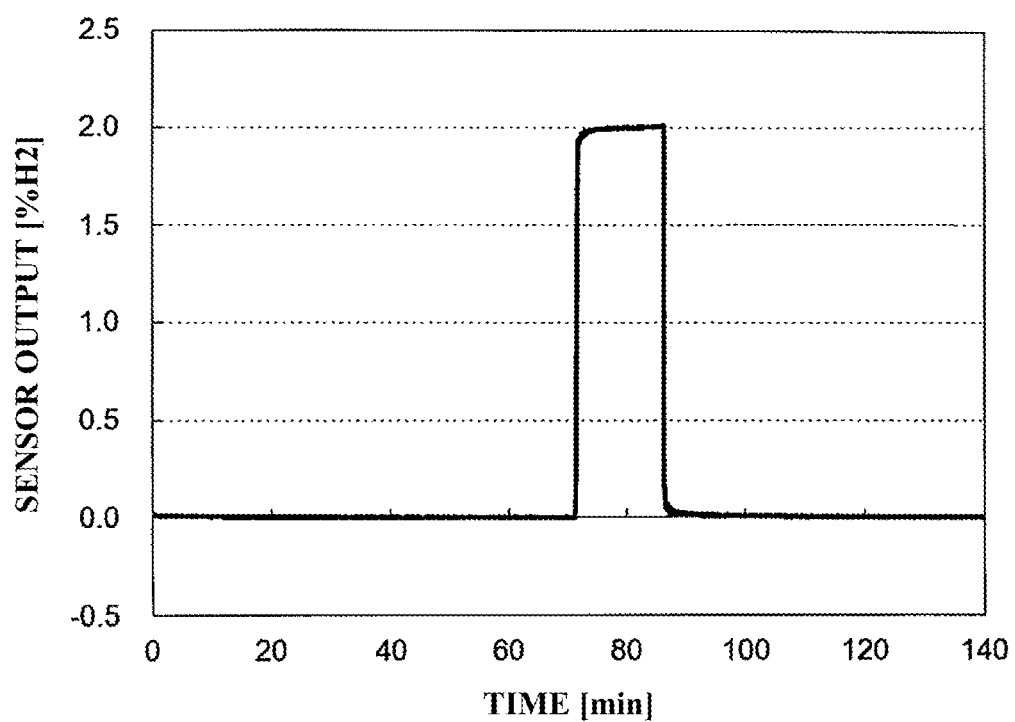
FIGS. 9 and 10 are graphs respectively showing changes in outputs of gas sensors according to Examples 2 and 1.
Figure 10:
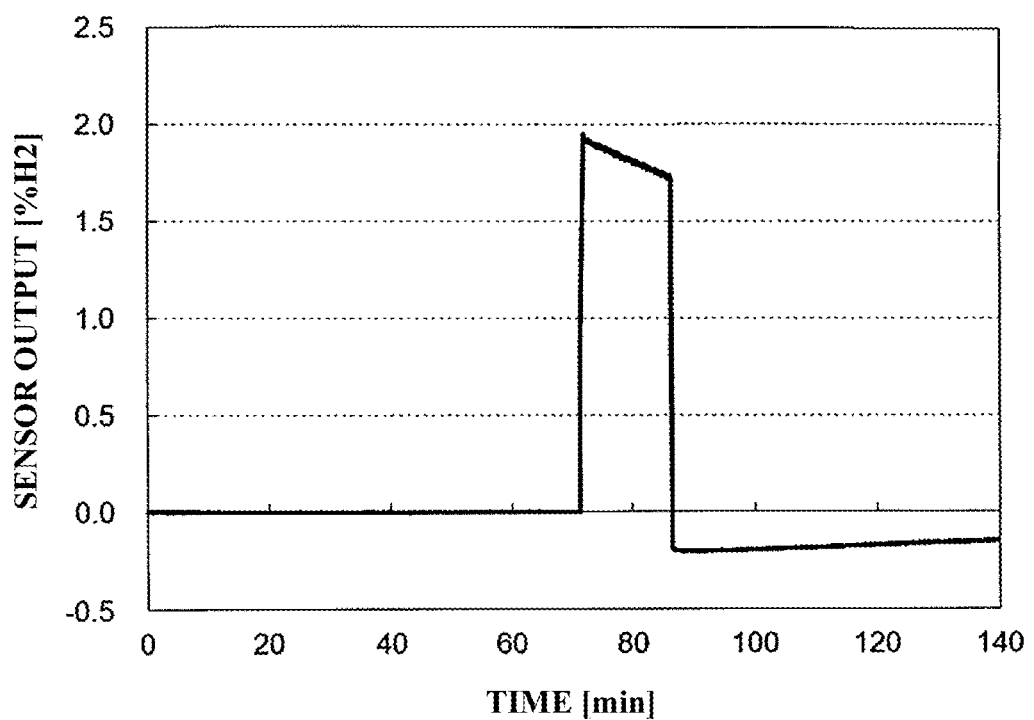

In Example 1, the output of the gas sensor 1 was deteriorated with time as shown in FIG. 10. In Example 2, by contrast, the output of the gas sensor 1 was maintained constant without deterioration as shown in FIG. 9. The output of the gas sensor 1 was more accurate in Example 2 where the gas sensor 1 was provided with the hydrogen oxidation catalyst 4D than in Example 1 where the gas sensor 1 was not provided with the hydrogen oxidation catalyst 4D.

2. Modification Examples

Although the present invention has been described with reference to the above embodiments, the above embodiments are intended to facilitate understanding of the present invention and are not intended to limit the present invention thereto. Various changes and modifications can be made to the above embodiments without departing from the scope of the present invention.

(2a) In the gas sensor 1, the mount base 7 and the protective cap 8 are not necessarily made of the same insulating ceramic material. Even when the mount base 7 and the protective cap 8 are made of different insulating ceramic materials, the effects of the present invention can be obtained because of a small difference in thermal expansion coefficient between the mount base 7 and the protective cap 8.

(2b) Although the first and second installation parts 4 and 5 are integrally formed by the common mount base 7 and the common protective cap 8 in the above embodiments, the first and second installation parts 4 and 5 may be formed as separate parts by providing the mount base 7 and protective cap 8 for the first installation part 4 separately from those for the second installation part 5. The first and second installation parts 4 and 5 may be located apart from each other.

Each of the first and second installation parts 4 and 5 is not necessarily formed by the mount base 7 and the protective cap 8 and may be formed by a single hollow structural member. In the case where the each of the first and second installation parts 4 and 5 is formed by the mount base 7 and the protective cap, the mount base 7 and the protective cap 8 are not necessarily adhered by the insulating adhesive 9A.

(2c) The membrane member 4C may alternatively be arranged outside the protective cap 8 so as to cover the first gas introduction hole 4B. Further, the membrane member 4C may be attached to the protective cap 8 by any means other than the insulating adhesive 9A.

(2d) It suffices that at least a portion of the first installation part 4 in contact with the membrane member 4C is made of an insulating ceramic material or resin material. In one modification example, the protective cap 8 may have a cap body made of a metal material and covered with a coating of insulating ceramic material or resin material.

(2e) The filter 6B is not necessarily provided in the casing 6. The shape of the casing 6 as shown in FIGS. 1 and 2 is a mere example and can be modified as appropriate.

(2f) In the gas sensor 1, each of the first and second sensor elements 2 and 4 may not be equipped with the temperature measuring resistor 24. Alternatively, the first and second installation parts 4 and 5 may be each provided with any temperature measuring means other than the temperature measuring resistor 24.

(2g) Furthermore, each of the first and second sensor elements 2 and 3 is not limited to the thermal conductivity type and may alternatively be in the form of a contact combustion type sensor element that causes combustion of the measurement target gas by a combustion catalyst (such as noble metal).

(2h) The hydrogen oxidation catalyst 4D may be arranged to cover the first gas introduction hole 4B without being located inside the first gas introduction hole 4B as shown in 8A.

Figure 8A:
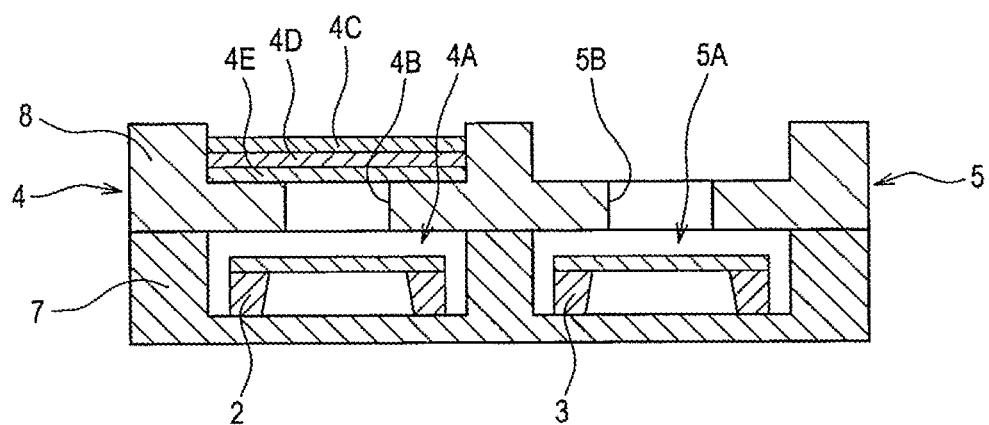
FIG. 8A is an enlarged cross-sectional of a part of a gas sensor in the vicinity of first and second installation parts according to a modification of the second embodiment of the present invention.

(2i) As shown in FIG. 8A, the first installation part 4 may have a sheet-shaped support member 4E that supports the membrane member 4C and the hydrogen oxidation catalyst 4D. In this case, the support member 4E is a porous gas-permeable body made of e.g. carbon material, ceramic material or the like. By such a support member 4E, it is possible to suppress warpage of the membrane member 4C and the hydrogen oxidation catalyst 4D and enhance the sealing of the first gas introduction hole 4B. Further, the membrane member 4C and the hydrogen oxidation catalyst 4D can be integrated together by the support member 4E as one sheet structure for improved handling. Although the support member 4E is laminated on a surface of the hydrogen oxidation catalyst 4D opposite from the membrane member 4C in FIG. 8A, the support member 4E may alternatively be laminated on a surface of the membrane member 4C opposite from the membrane member 4C.

Figure 8B:
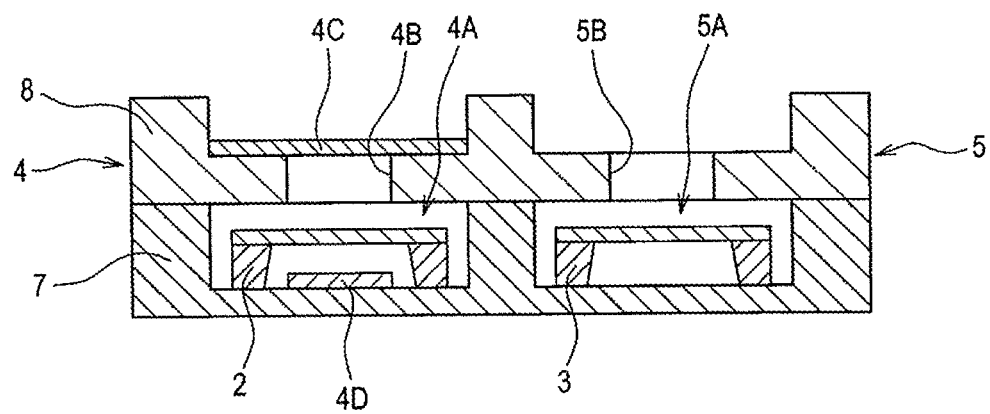
FIG. 8B is an enlarged cross-sectional of a part of a gas sensor in the vicinity of first and second installation parts according to another modification of the second embodiment of the present invention.

(2j) The hydrogen oxidation catalyst 4D is not necessarily arranged to cover the first gas introduction hole 4B. For example, the hydrogen oxidation catalyst 4D may be arranged on an inner wall of the first installation part 4 in which the first gas introduction hole 4B is defined. The hydrogen oxidation catalyst 4D is not also necessarily arranged inside the first gas introduction hole 4B. For example, the hydrogen oxidation catalyst 4D may be arranged inside the first inner space 4A as shown in FIG. 8B. Furthermore, the hydrogen oxidation catalyst 4D is not necessarily sheet-shaped.

(2k) The hydrogen oxidation catalyst 4D is not necessarily arranged between the membrane member 4C and the first inner space 4A or inside the first inner space 4A. For example, the hydrogen oxidation catalyst 4D may be laminated between two membrane members 4C or may be dispersed and included in the membrane member 4C.

(2l) In the above embodiment, it is feasible to divide the function of one component among a plurality of components or combine the functions of a plurality of components into one. Any of the technical features of the above embodiments may be omitted, replaced or combined as appropriate. All of embodiments and modifications derived from the technical scope of the following claims are included in the present invention.

The entire contents of Japanese Patent Application No. 2017-149988 (filed on Aug. 2, 2017) and No. 2018-054440 (filed on Mar. 22, 2018) are herein incorporated by reference.

What is claimed is:

1. A gas sensor for detecting a measurement target gas in a measurement gas atmosphere, comprising:
    a first sensor element;
    a first installation part defining a first inner space in which the first sensor element is installed; and
    a casing accommodating therein the first installation part, the casing having an opening formed to introduce the measurement target gas into an inside of the casing,
    the first installation part having: a first gas introduction hole formed to provide communication between the first inner space and the inside of the casing; and a membrane member arranged to cover the first gas introduction hole and having permeability to water vapor and substantially no permeability to the measurement target gas,
    wherein at least a portion of the first installation part in contact with the membrane member is made of insulating ceramic material or resin material,
    wherein the first installation part further comprises a measurement target gas oxidation catalyst arranged between the membrane member and the first inner space or inside the first inner space to cause oxidation of the measurement target gas flowing into the first inner space.

2. The gas sensor according to claim 1,
wherein the first installation part is made of an insulating ceramic material.

3. The gas sensor according to claim 2,
wherein the first installation part is constituted by: a mount base made of an insulating ceramic material so as to mount thereon the first sensor element; and a protective cap made of an insulating ceramic material and disposed on the mount base so as to cover the mount base and define the first inner space between the mount base and the protective cap, and
wherein the mount base and the protective cap are bonded together by an insulating adhesive.

4. The gas sensor according to claim 3,
wherein the mount base and the protective cap are made of the same insulating ceramic material.

5. The gas sensor according to claim 3,
wherein the insulating adhesive contains a thermosetting resin as a main component.

6. The gas sensor according to claim 3, further comprising:
a second sensor element; and
a second installation part accommodated in the casing and defining a second inner space in which the second sensor element is installed,
wherein each of the first and second sensor elements has a heating resistor whose resistance value varies with change in temperature thereof, and
wherein the second installation part has a second gas introduction hole formed to allow direct introduction of the measurement target gas from the inside of the casing into the second inner space.

7. The gas sensor according to claim 6,
wherein the second installation part is constituted by the mount base and the protective cap, so that the second sensor element is mounted on the mount base, and, so that the protective cap is disposed on the mount base so as to cover the mount base and define the second inner space between the mount base and the protective cap.

8. The gas sensor according to claim 1,
wherein the membrane member is an ion exchange membrane made of fluororesin.

9. The gas sensor according to claim 1,
wherein the measurement target gas oxidation catalyst is arranged inside the first gas introduction hole.

10. The gas sensor according to claim 1,
wherein the measurement target gas oxidation catalyst is arranged to cover the first gas introduction hole.

11. The gas sensor according to claim 10,
wherein the measurement target gas oxidation catalyst is sheet-shaped and arranged on a first inner space-side surface of the membrane member.

12. The gas sensor according to claim 11,
wherein the first installation part comprises a sheet-shaped support member that supports at least one of the membrane member and the measurement target gas oxidation catalyst.

* * * * *